US005753714A

United States Patent [19]
Stemerick et al.

[11] Patent Number: 5,753,714
[45] Date of Patent: May 19, 1998

[54] POLYAMINE DERIVATIVES

[75] Inventors: David M. Stemerick, Fairfield; Alan J. Bitonti, Maineville; Michael L. Edwards, Cincinnati; Peter P. McCann, Cincinnati; Albert Sjoerdsma, Cincinnati, all of Ohio

[73] Assignee: Merrell Pharmaceuticals Inc., Cincinnati, Ohio

[21] Appl. No.: 213,386

[22] Filed: Mar. 15, 1994

Related U.S. Application Data

[63] Continuation of Ser. No. 840,573, Feb. 24, 1992, abandoned, which is a continuation of Ser. No. 678,892, Mar. 28, 1991, abandoned, which is a continuation of Ser. No. 499,559, Mar. 26, 1990, abandoned, which is a continuation of Ser. No. 295,721, Jan. 10, 1989, abandoned, which is a continuation-in-part of Ser. No. 229,086, Aug. 5, 1988, abandoned, which is a continuation-in-part of Ser. No. 10,380, Feb. 3, 1987, abandoned.

[51] Int. Cl.$^6$ ............... A61K 31/135; C07C 211/43
[52] U.S. Cl. .............. 514/654; 514/655; 564/367
[58] Field of Search ................... 564/337, 367, 564/374, 512; 514/649, 654, 674, 561, 564, 565

[56] References Cited

U.S. PATENT DOCUMENTS

| | | | |
|---|---|---|---|
| 2,267,204 | 12/1941 | Kyrides | 564/512 |
| 2,279,294 | 4/1942 | Hardman | 564/367 X |
| 2,317,757 | 4/1943 | Graf | 564/367 X |
| 2,624,759 | 1/1953 | Bersworth | 564/367 X |
| 2,627,491 | 2/1953 | Szabo et al. | 564/272 |
| 2,653,977 | 9/1953 | Craig et al. | 564/367 |
| 2,770,653 | 11/1956 | Haslick et al. | 564/370 |
| 3,013,020 | 12/1961 | Fancher | 564/511 |
| 3,369,905 | 2/1968 | Jones et al. | 564/367 X |
| 3,689,646 | 9/1972 | Sevag | 564/512 |
| 3,697,659 | 10/1972 | Marco | 514/673 |
| 3,912,816 | 10/1975 | Hofmann et al. | 514/674 |
| 3,933,913 | 1/1976 | Colella et al. | 564/374 |
| 4,010,200 | 3/1977 | Kalopissis et al. | 564/367 |
| 4,014,937 | 3/1977 | Richardson | 564/374 |
| 4,048,324 | 9/1977 | Kohn | 514/500 |
| 4,058,624 | 11/1977 | Jacobus et al. | 564/374 |
| 4,092,432 | 5/1978 | Bjorklund et al. | 564/512 |
| 4,172,094 | 10/1979 | Dybas et al. | 564/337 |
| 4,182,849 | 1/1980 | Ezzell | 528/392 |
| 4,258,061 | 3/1981 | Gronin et al. | 564/374 |
| 4,311,709 | 1/1982 | Dybas et al. | 564/337 |
| 4,321,190 | 3/1982 | Costanzi et al. | 524/252 |
| 4,322,530 | 3/1982 | Jachimowicz | 564/307 X |
| 4,499,072 | 2/1985 | Sunkara et al. | 424/85.7 |
| 4,505,861 | 3/1985 | Bergeron, Jr. | 564/512 X |
| 4,507,321 | 3/1985 | Raisfeld | 564/512 X |
| 4,559,362 | 12/1985 | Umezawa et al. | 514/674 |
| 4,591,605 | 5/1986 | Ray | 514/579 |
| 4,719,313 | 1/1988 | Gerhart et al. | 564/512 |
| 5,013,760 | 5/1991 | Farmer et al. | 514/649 |
| 5,091,576 | 2/1992 | Bergeron | 564/367 |
| 5,109,024 | 4/1992 | Prakash et al. | 514/674 |

FOREIGN PATENT DOCUMENTS

| | | |
|---|---|---|
| 0161459 | 11/1985 | European Pat. Off. . |
| 0162413 | 11/1985 | European Pat. Off. . |
| 162413 | 11/1985 | European Pat. Off. ............... 514/674 |
| 0270349 | 6/1988 | European Pat. Off. . |
| 0277635 | 8/1988 | European Pat. Off. . |
| 0311068 | 4/1989 | European Pat. Off. . |
| 2335208 | 7/1977 | France . |
| 2262333 | 7/1974 | Germany . |
| 2557657 | 6/1977 | Germany . |
| 3326723 | 4/1982 | Germany . |
| 2458222 | 2/1984 | Germany . |
| 7007521 | 4/1966 | Japan . |
| 52-118405 | 10/1977 | Japan . |

OTHER PUBLICATIONS

Bergeron, "Acc. Chem. Res.", vol. 19, pp. 105–113(1986) (I).
A. Lehninger, "Biochemistry" 2nd Ed., pp. 716–718, Worth Publishers, Inc., New York (1975).
Brown et al, "Fungicidal Activity and Chemical Constitution XXI. The Fungatoxicity of Aliphatic Polyamines", Pest. Sci. (1983), 4, 485–490.
Chem. Abstr. #116(23): 227654d of Farmaco, 46 (10), 1167–78, Minarini et al, "Further Investigation on Methotramine–Related Tetraamines" (1991).
Chem. Abstr. #113(11): 97320s of Arch. Pharm. (Weinheim, Ger.), 323(5), 287–94, Rehse et al, Platelet Aggregation Inhibiting and Anticoagulant Effects of Oligoamines (1990).
Chem. Abstr. #88(5): 32006g of Acta Med. Scand., Suppl., 606, 95–100, Clark B.J., "Dopamine Receptor Stimulants in Hypertension", (1976).
Chem. Abstr. #83(19): 163798u of Ger. Offen., 15 pp., Pless J. "Phenylethylamine Derivatives", (1975).
Edwards et al, "Polyamine Analogues with Antitumor Activity", J. Med. Chem., vol. 33, pp. 1369–1375, 1990.
Edwards, M.L., et al., J. Med. Chem., 34, 2414–2410 (1991).
Bitonti, A.J., et al, Biochem. J., 257, 769–774 (1989).
Work, T.S., J.Chem.Soc. 1940, 1315, 1940.
Goodson, J.A., et al., Brit.J.Pharmacol. 3, 49–61, 1948.
Roe, A.M., et al., J.Chem.Soc.(C) Org. 527–530, 1966.
Brown, D., et al., Pestic.Sci., 4, 485–490, 1973.
van Alphen, J., Rec. Trav. Chim. 59: 31–40, 1940.
van Alphen, J., Rec. Trav. Chim. 58: 544–9, 1939.
Israel, M., et al., J. Med. Chem. 7, 710–716, 1964.
Israel, M., et al., J. Med. Chem. vol. 14, No. 11, 1042–1047, 1971.
Weinstock, L.T., et al., J. Pharm. Sci. 70, 956–959, 1981.

(List continued on next page.)

Primary Examiner—Deborah Lambkin
Attorney, Agent, or Firm—Louis J. Wille; David M. Stemerick

[57] ABSTRACT

This invention relates to certain polyamine derivatives, to the methods and intermediates useful for their preparation, and to their use in treating diseases caused by infestation with a variety of parasitic protozoa.

31 Claims, No Drawings

OTHER PUBLICATIONS

Stevens, L., Biochem. J. 103, 811–815, 1967.

Clay, R.M., et al., Inorg. Chem. 24(21), 3330–6, 1985 as abstracted in Chemical Abstracts 103, No. 16, Oct. 85, p. 703, No. 133893K.

MArkovitsi, D. et al., Nouv. J. Chim. 5(3), 141–7, 1981 as abstracted in Chem Abstracts 94, 214950z.

Takahashi, M., et al., J. Biochem. 100(1), 123–31, 1986 as abstracted in Chem. Abstracts 105, 167691.

Weitl, F.L., et al., J. Org. Chem. 46, 5234–5237, 1981.

Melchiorre, C., et al., J. Med. Chemistry vol. 21, No. 11, 1126–1132, 1978.

Brasili, L., et al., Life Sciences vol. 38, pp. 1633–1640, 1986.

Goto, M. et al., Inorg. Chem. 9(6), 1488–96, 1970 abstracted in Chemical Abstracts 73 No. 4, Jul. 1970, p. 462, No. 20934t.

Melchiorre, C., et al., J. Med. Chem. 30, 201–204, 1987.

van Alphen, J., Rec. Trav. Chim. 58, 1105–8, 1939, as abstracted in Chemical Abstracts vol. 34, 2331, 1940.

Lehninger, A. L., Biochemistry, Second Edition, 716–718, 1975.

Baumann, R. J., et al., Antimicrobial Agents and Chemotherapy, pp. 722–727, May 1990.

Bitonti, Alan J. et al., Biochem. J. 257, 769–774, 1989.

Bitonti, A.J., Biochem. Pharm.Short Communication, 1989.

Assef, G., et al., Bulletin de la Societe Chimique de France, No. 3–4, II–165–176, 1979.

POLYAMINE DERIVATIVES

This is a continuation of application Ser. No. 07/840,573, filed Feb. 24, 1992, now abandoned; which is a continuation of application Ser. No. 07/678,892, filed Mar. 28, 1991, now abandoned; which is a continuation of application Ser. No. 07/499,559, filed Mar. 26, 1990, now abandoned; which is a continuation of application Ser. No. 07/295,721, filed Jan. 10, 1989, now abandoned; which is a continuation-in-part of application Ser. No.07/229,086, filed Aug. 5, 1988, now abandoned; which is a continuation-in-part of application Ser. No.07/010,380, filed Feb. 3, 1987, now abandoned.

This invention relates to certain polyamine derivatives, to the methods and intermediates useful for their preparation, and to their use in treating diseases caused by infestation with a variety of parasitic protozoa.

More specifically, this invention relates to the treatment of a variety of disease states caused by parasitic protozoa infesting warm-blooded animals, the treatment being the administration to the host suffering from these diseases an antiprotozoal amount of a polyamine derivative of the formula:

$$RHN(CH_2)_nNH(CH_2)_mNH(CH_2)_nNHR$$

and the pharmaceutically acceptable salts thereof, wherein n is an integer 2 to 6, m is an integer 3 to 12, and R is a $C_1$–$C_6$ saturated or unsaturated hydrocarbyl radical or —$(CH_2)_x$—(Ar)—X wherein:

x is zero, one or two,

Ar is phenyl or naphthyl, and

X is H, $C_1$–$C_6$ alkoxy, halogen, $C_1$–$C_4$ alkyl, —$S(O)_xR_1$ with $R_1$ being $C_1$–$C_6$ alkyl, said administration to the infected host being with or without conjunctive therapy with an ornithine or arginine decarboxylase inhibitor.

In those instances wherein R is a saturated hydrocarbyl such compounds include those straight, branched or cyclized manifestations of alkyl radicals having up to six carbon atoms, with ethyl, t-butyl and cyclohexyl being preferred. When R is an unsaturated hydrocarbyl moiety such moieties include those radicals having one or two double bonds and those having one triple bond which may be represented by such preferred radicals as —$CH_2CH=CH_2$, —$CH_2CH_2CH=CH_2$, —$CH_2C\equiv CH$, —$CH_2CH=C=CH_2$. Optionally such radicals may bear a phenyl or naphthyl moiety such as, for example, ØCH=CHCH$_2$—. In those instances defined by the moieties $(CH_2)_n$, wherein n is 2 to 6, such moieties include straight and branched alkyl radicals having up to six carbon atoms, preferably ethylene, propylene, and butylene as straight chain alkylene moieties, although these may be branched chain moieties. In those instances defined by the $(CH_2)_m$ moiety wherein such moieties include straight and branched alkylene moieties having up to 12 carbon atoms, the preferred moieties contain 5, 6, 7, 8 or 9 carbon atoms (preferably straight chain). In those instances defined by —$(CH_2)_x$—(Ar)—X, it is preferred that x be one or two, Ar be unsubstituted phenyl or naphthyl, but when substituted it is preferred that the alkoxy radical be methoxy or ethoxy, the halo be chloro, the alkyl radical be methyl, ethyl or t-butyl and when $S(O)_nR_1$, it is preferred that $R_1$ be methyl, ethyl or t-butyl and that n be either zero, one or two. In any particular compound defined by formula I, it is preferred that such compounds be symmetrical in their makeup. For example, it is preferred that for each individual compound each terminal R group be the same, and that each $(CH_2)_n$ moiety be the same.

For ease in discussing and describing the concepts of this application it is convenient to use certain abbreviated forms for referring to either generic or types of compounds. For example, the compound 1,18-bis-[(phenyl)methyl]-1,5,14,18-tetraazaoctadecane of the structure ØCH$_2$NH(CH$_2$)$_3$NH (CH$_2$)$_8$NH(CH$_2$)$_3$NHCH$_2$Ø would, in its abbreviated version, be shown as BnNH(3)NH(8)NH(3)NHBn, (Bn being benzyl), and also may be referred to as a bis-benzyl-3-8-3 compound, the nitrogen atoms obviously being understood. In the event unsymmetric compounds are employed they would be referred to as, e.g., N-benzyl-N'-phenethyl-3-8-4.

In general, the compounds of formula I may be prepared by chemical reactions analogously known in the art, the choice of any specific route of preparation being dependent upon a variety of factors. For example, general availability and cost of the reactants, applicability of certain generalized reactions to specific compounds, presence of unsaturated hydrocarbyl moieties, and so forth, are all factors which are fully understood by those of ordinary skill in the art and all contribute to the choice of synthesis in the preparation of any specific compound embraced by formula I.

With the foregoing in mind, the following reaction schemes are illustrative of the pathways by which the compounds of this invention may be made.

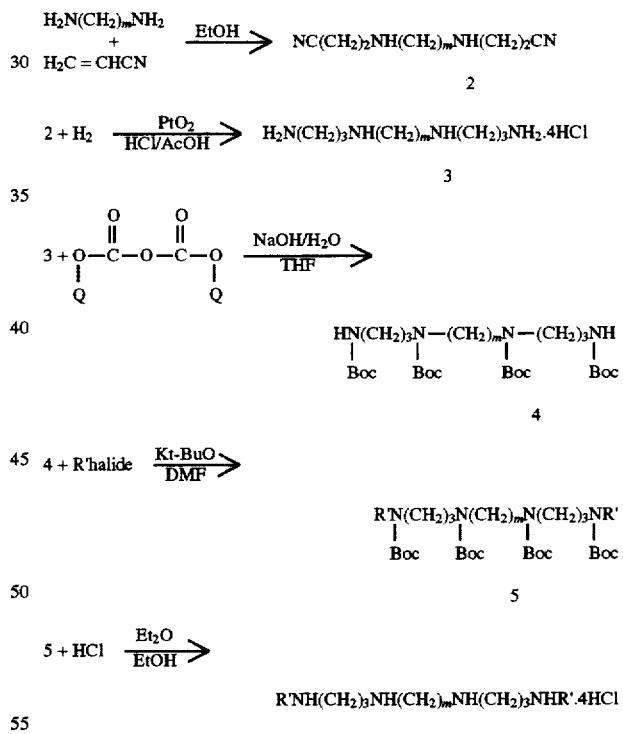

wherein R' is as defined for R in formula I except that when R is X—(Ar)13 CH$_2$)$_x$, x cannot be zero, Boc is the t-butoxycarbonyl protecting group, and Q is tert-butyl.

In the foregoing five step process the initial step entails a specific N-alkylation designed to produce compounds wherein n is 3 and which entails the reaction of a diamine (wherein m is as generically defined in formula I) with 2 equivalents of acrylonitrile by heating reactants, either in a suitable solvent or neat, according to standard conditions well known in the art. The resulting cyano derivatives (2) are chemically reduced by reaction with hydrogen in the presence of a catalyst ($PtO_2$) in a suitable solvent with 8 equivalents of hydrochloric or hydrobromic acid to produce the resulting hydrohalic salts according to standard procedures well known in the art. Of course other reducing systems, e.g., reduction with lithium aluminum hydride, may also be utilized to produce compounds of formula 3. Following the preparation of these compounds the hydroholic salts are neutralized with base and the nitrogen atoms are protected, preferably with di-t-butyldicarbonate according to standard operating conditions. The tetra N-protected amines (5) are alkylated with the appropriate alkyl or as alkyl halides (chloro or bromo) by reaction in the presence of potassium butoxide according to standard alkylation procedures well known in the art. Following alkylation the N-protective groups are removed by standard procedures, e.g., treatment with acid, preferably HCl, in the presence of a suitable solvent or solvent system, e.g., diethyloxide in ethanol, to obtain the desired products (6).

Alternatively compounds of formula 3 may be subjected to a reductive alkylation using an appropriate aldehyde (except the aldehyde cannot bear an alkylthio substituent); the reduction being effected by hydrogenation in the presence of $PtO_2$ according to well known procedures. This procedure does not require protection of the nitrogen atoms of the intermediates. In those instances wherein the desired final products do bear an alkylthio moiety of an unsaturated hydrocarbyl radical on the terminal nitrogen atoms, the compounds 3 (and their otherwise-prepared homologs, i.e., n is 2, 3 or 4) may be subjected to a reductive alkylation using an appropriate aldehyde but wherein the reduction is effected with sodium cyanoborohydride according to standard techniques, this reductive alkylation again not requiring the protection of the nitrogen atoms of the intermediates.

A preferred route for the preparation of compounds of formula I wherein n is four (but which can also be applicable to those compounds wherein n is 2 to 6) and are otherwise analogous to those compounds identified as (6) in Reaction Scheme A, is the following Reaction Scheme B.

Reaction Scheme B

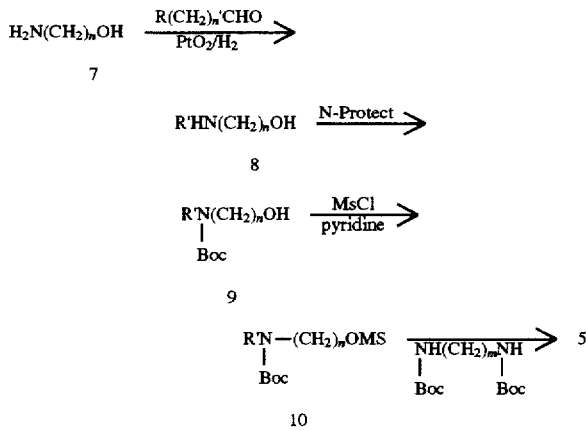

wherein n is primarily 4, but could be 2 to 6, Boc is the t-butoxycarbonyl nitrogen protecting group (which is preferred but which can be modified to any suitable N-protecting group), R' is X—(Ar)—($CH_2$)$_x$ with x being other than zero, and Ar' is an X-substituted alkyl or aryl (as defined in formula I), n' is zero or a positive integer, and Ms is mesyl.

This reaction is initiated by reductive alkylation techniques using an amino alcohol (7) and an appropriate aldehyde to form R' substituted amino alcohols (8) which are N-protected. The N-protected amino alcohols (9) are converted to their mesylates (10) by standard reaction conditions, e.g., reaction with mesylchloride in the presence of pyridine, preferably in the presence of a solvent such as $CH_2Cl_2$.

The mesylate is subjected to alkylation with an N-protected diamine (i.e., BocNH($CH_2$)$_m$NHBoc) using potassium t-butoxide in a solvent (DMF) using standard procedures. The so-produced tetra N-protected tetramines (5) are deprotected as in Scheme A. In essence the foregoing reductive alkylation, N-protection, mesylation, alkylation and deprotection procedures all employ techniques and reaction conditions which are well known in the art.

In those instances wherein it is desired to prepare compounds of formula I wherein n is 2, it is preferred to employ Reaction Scheme C to obtain the necessary intermediates (13) which intermediates would be subject to the alkylation procedures discussed above in Scheme A.

Reaction Scheme C

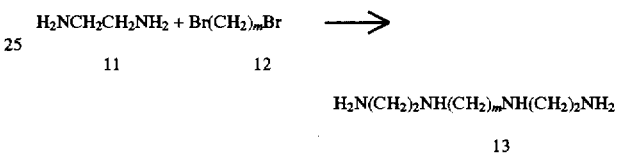

wherein m is as defined in formula I.

The foregoing N-alkylation entails the reaction of an appropriate dihaloalkane (12) with excess quantities (10X) of ethylene diamine (11) by heating the reactants at reflux temperatures in a suitable solvent, e.g., ethanol. Preferably, preparation of the desired final products bearing the R substituents on the terminal nitrogen atoms of intermediates (13) may be effected by the reductive alkylation procedures using appropriate aldehydes without N-protecting groups as alternatively discussed under Reaction Scheme A, or the intermediates (13) may just be N-protected, alkylated, and deprotected by methods analogous to the depicted step 3, 4 and 5 of Reaction Scheme A.

A preferred method for preparing compounds wherein Ar represents phenethyl (or naphthylethyl), (particularly wherein n is 3 and m is 8) is the reaction of an aroyl-chloride according to the method depicted in the following Reaction Scheme D.

Reaction Scheme D

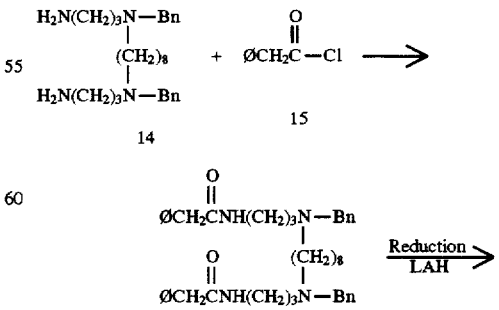

-continued
Reaction Scheme D

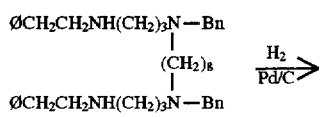

17

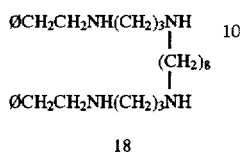

18 wherein Bn is benzyl, Ø is phenyl and LAH is lithium aluminum hydride. As stated above, the foregoing reaction is a preferred method for the preparation of one particular compound which entails N-alkylation of a partially protected intermediate (14) with an arylacetyl chloride (15) in the presence of triethylamine, using an inert solvent, to form an amide (16) which is chemically reduced, preferably with lithium aluminum hydride, and the resulting product (17) catalytically (H₂,Pd/C) de-benzylated to form the desired end product. These steps entail reaction techniques and procedures well known and understood in the art. Of course the same reaction scheme can be applied for the preparation of other compounds of formula I; adoption of the technique being with the usual caveats well understood by those of ordinary skill in the art.

In those instances wherein Ar represents an aromatic moiety (X-phenyl or X-naphthyl) which is attached directly to the terminal nitrogen atoms (i.e., x is zero) then such compounds may be prepared according to the general reactions of Reaction Scheme E, as follows:

Reaction Scheme E

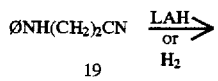

19

ØNH(CH₂)₃NH₂ —N-Protection→

20

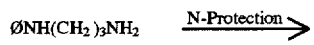

21

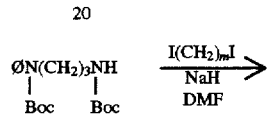

22

The foregoing reaction scheme depicts the preparation of compounds wherein Ar is phenyl, the first step of which is a lithium aluminum hydride reduction effected according to procedures published in the art (Bul. Soc. Chim. Fr., Part 2, 165–7 (1979)). Of course this reaction scheme can be expanded to include naphthyl and X-substituted intermediates which will not be adversely affected by the reaction conditions. Preferably the N-protection uses the t-butoxycarbonyl protecting groups which are put on and taken off according to standard techniques already mentioned hereinabove. The N-protected compounds are alkylated by reaction with an appropriate dihalo alkane using standard and well known procedures.

In those instances wherein it is desired to prepare compounds of formula I which contain an unsaturated hydrocarbyl moiety, i.e., acetylenic, allenic or allylic moiety-containing compounds, it is preferred to use the techniques of Reaction Scheme F, as follows:

Reaction Scheme F

23

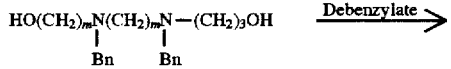

24

HO(CH₂)ₙNH(CH₂)ₘNH(CH₂)₃OH —N-Protect→

25

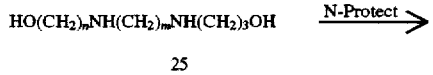

26

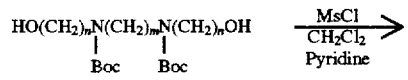

27

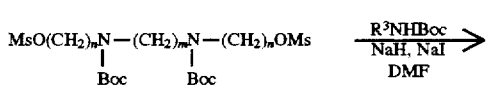

29

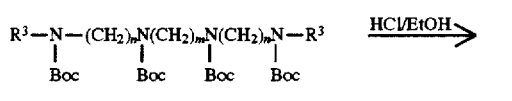

30 wherein R³ is an appropriate unsaturated hydrocarbyl moiety, Bn is benzyl, MsCl is methanesulfonyl chloride and Boc is the t-butoxycarbonyl protecting group.

In the foregoing reaction a dibenzylated diamine (23) is N-alkylated by a simple displacement reaction to form compounds (24) which are sequentially benzylated and N-protected. These steps are effected according to well known and standard procedures. The resulting bis(hydroxy)-aminoalkanes (26) are mesylated and the mesylates (27) are alkylated with two equivalents of an N-protected amine bearing an appropriate unsaturated hydrocarbyl moiety, e.g., N-(t-butoxycarbonyl)-2,3-butadienylamine. A so-obtained tetra protected tetramine (29) is then readily de-protected to produce the desired compounds (30).

In those instances wherein it is desired to convert an alkylthio substituent to one of its higher oxidation states the alkyl thioether is treated with a peracid according to known conditions. Suitable oxidizing agents are H₂O₂ and NaIO₄ but meta-chloroperoxybenzoic acid is preferred. In effecting the oxidation to a sulfinyl derivative 1 molar equivalent (per alkylthioether moiety) is used and 2 molar equivalents of the peracid will yield the sulfonyl derivatives. The oxidations are effected at temperatures of about 0° C. to room temperature in solvents which themselves are not susceptible to

7 oxidation. Preferred solvents are $CH_2Cl_2$, $CHCl_3$, acetic acid and ethyl acetate.

Illustrative Examples for Reaction Scheme A

EXAMPLE 1

1.18-Bis[(phenyl)methyl]1,5,14,18-tetraazaoctadecane●4HCl

Step A: N,N'-Bis-[2,2'-bis(cyano)ethyl]-1,8-diamino-octane

Dissolve 28.8 gm (0.2 mol) of 1,8 diaminooctane in 250 ml of EtOH. Add 27 ml (0.41 mol) of acrylonitrile and gently reflux the mixture overnight. Remove the solvent at reduced pressure. Analysis shows desired material to be >95% pure.

Step B: 1,5,14,18-Tetraazaoctadecane tetrahydrochloride

Combine 50.0 gm of the product of Example 1, 2.0 gm $PtO_2$, 133 ml of conc. HCl at 45 lbs./sq.in. in a shaker flask until hydrogen is no longer taken up. Filter the resulting mixture, evaporate the solvent and triturate the product with 1 liter of EtOH. Filter and dry the product to obtain 51.6 gm of the title compound. Rf is 0.17 (silica gel plates eluted with 40% conc. $NH_3/CH_3OH$).

Step C: 1,5,14,18-Tetra(t-butoxycarbonyl)-1,5,14,18-tetraazaoctadecane

Treat 28.0 gm (0.069 mol) of the product of Step B with 10.99 gm (0.274 mol) of NaOH in 120 ml $H_2O$. When a homogenous solution is obtained add 65.7 gm (0.307 mol) of di-t-butyldicarbonate in 750 ml of THF and stir the resulting mixture for 16 hours. Separate the layers, remove and wash (2×) the aqueous layer with 500 ml $CH_2Cl_2$. Combine and dry ($MgSO_4$) the organics, filter and evaporate (in vacuo) the solvents and flash chromatograph the residue (silica gel), eluting with 25% EtOAc/hexane to yield 30.2 g of the desired product. Rf is 0.33 on silica gel plates eluted with 25% EtOAc/hexane).

Step D: 1,18,-Bis[(phenyl)methyl]-1,5,14,18-tetra(t-butoxycarbonyl)-1,5,14,18-tetraazaoctadecane Dissolve 20.0 gm (0.03 mol) of the product from Step C in 30 ml DMF and treat with 7.5 gm (0.067 mol) KtBuO and 7.96 ml (0.067 mol) BnBr, with stirring for 18 hours. Evaporate the volatiles (0.5 mm and 45° C.) and take up the resulting residue in 1400 ml of EtOAc and water-wash (2×, 500 ml). The organic layer is then dried ($MgSO_4$) and the solvent is evaporated (in vacuo). Flash chromatography on silica gel eluted with 20% EtOAc/hexane yields 12.4 gm (50%) of desired product as a clear viscous oil. Rf is 0.42 (silica gel plates eluted with 25% EtOAc/hexane).

Step E: 1,18-Bis-[(phenyl)methyl]-1,5,14,18-tetraazaoctadecane4●HCl

Dissolve 12.4 g (0.0147 mol) of the product of Step D in 14.7 ml of anhydrous EtOH and treat with 160 ml of 2N HCl in $Et_2O$ with stirring overnight. Filter, wash the filter cake with $Et_2O$, and dry to obtain 7.2 gm of the desired compound, mp >300° C. Rf is 0.24 (from silica gel eluted with 10% conc. $NH_3/CH_3OH$).

EXAMPLE 1A 1,18-Bis[(phenyl)methyl]1,5,14,18-tetraazaoctadecane●4HCl

Steps A and B: 1,5,13,17-Tetraazaheptadecane tetrahydrochloride

Prepare the title compound by the method of Israel et al., J. Med. Chem. 7, 710 (1964).

Step C: 1,5,13,17-Tetra(t-butoxycarbonyl)-1,5,14,18-tetraazaheptadecane

Combine 1,5,13,17-tetraazaheptadecane tetrahydrochloride (3.9 gm, 0.01 mol) and sodium hydroxide (1.76 gm, 0.44 mol) in water (44 ml) and stir until homogeneous. To this mixture add di-t-butyldicarbonate (9.6 gm, 0.044 mol) in THF (88 ml) and stir for 3 hours. Dilute the mixture with ethyl acetate (EtOAc) [300 ml] and separate the organic layer. Dry the organic layer over anhydrous $MgSO_4$ and evaporate in vacuo to obtain a viscous oil. Purify the residue by flash chromatography (silica gel) eluting with 25% EtOAc/hexane to yield 3.0 gm of the title compound. Rf is 0.20 on silica gel plates eluted with 25% EtOAc/hexane.

Step D: 3,7,15,19-Tetra(t-butoxycarbonyl)-3,7,15,19-tetraazaheneicosane

Combine 1,5,13,17-tetra(t-butoxycarbonyl)-1,5,14,18-tetraazaheptadecane (3.0 gm, 0.0046 mol) and sodium hydride (50% in oil) [0.45 gm, 0.011 mol] in DMF (9 ml) and stir the mixture until hydrogen evolution ceases. Add ethyl iodide (0.9 ml, 0.011 mol) and stir the mixture for 18 hours. Evaporate the DMF in vacuo and partition the residue between ethyl acetate (600 ml) and water (200 ml). Separate the organic layer, dry the organic layer over anhydrous $MgSO_4$ and evaporate in vacuo. Purify the residue by flash chromatography (silica gel) eluting with 20% EtOAc/hexane to yield 1.68 gm of the title compound. Rf is 0.5 on silica gel plates eluted with 25% EtOAc/hexane.

Step E: N,N'-Bis[3-(ethylamino)propyl]-1,7-heptanediamine Treat 3,7,15,19-tetra(t-butoxycarbonyl)-3,7,15,19-tetraazaheneicosane (1.68 gm, 0.0024 mol) with HCl in methanol (50 ml, 1.0N) and stir overnight. Filter the mixture and recrystallize the title compound from methanol/water (20:80, v/v) to yield 0.5 gm of the title compound. Rf is 0.39 on silica gel plates eluted with 40% ammonia (concentrated) in methanol; mp 322-23° C. with degradation.

EXAMPLE 2

1,18-Bis(butyl)-1,5,14,18-tetraazaoctadecane●4HCl

Step A: 1,18-Bis-(butyl)-1,5,14,18-tetra(t-butoxycarbonyl)-1,5,14,18-tetraazaoctadecane Combine 3.5 gm (0.0053 mol) of the product of Step C of Example 1, 2.7 gm (0.024 mol) of KtBuO, 2.57 ml (0.024 mol) of 1-iodobutane in 10 ml of DMF and allow the mixture to stir for 18 hours. Evaporate the volatiles (0.5 mm at 45° C.), dissolve the residue in 500 ml of EtOAc, water-wash (2× with 100 ml) the organic layer and dry the organic layer over $MgSO_4$. Evaporate off the solvents and subject the residue to flash chromatography (silica gel eluted with 20% EtOAc/hexane to yield 1.32 gm of the title compound. Rf is 0.36 (silica gel plates eluted with 20% EtOAc/hexane).

Step B: Dissolve 1.32 gm (0.0017 mol) of the product of Step A of this example in 1.7 ml of EtOH, treat with 17 ml of 2N HCl in $Et_2O$ and stir the mixture overnight. Filter and wash the precipitate with $Et_2O$, recrystallize the washed material from isopropanol/water. Filter and dry the crystals ($P_2O_5$ at 79° C. at 0.1 mm) to yield 0.62 gm of the title compound, mp >300° C. Rf is 0.47 (silica gel plates eluted with 20% conc. $NH_3/CH_3OH$).

EXAMPLE 2A 1,18-[(1-Naphthyl)methyl]-1,5,14,18-tetraazaoctadecane tetrahydrochloride hemihydrate Step A: A solution of 1-chloromethylnaphthalene (1.7 g - 9.6 mmol) in 5 ml hexamethylphosphorous triamide (HMPA)

is added to a mixture of 1,5,14,18-tetra(t-butoxycarbonyl)-1,5,14,18-tetraazaoctadecane (2.6 g) and potassium t-butoxide (1.07 gm) in HMPA (50 ml). The mixture is heated in an 80° C. oil bath for 4 hours, poured into 300 ml of water, and the aqeuous mixture is extracted with ethyl acetate (2×300 ml). The combined extracts are extracted with water (3×300 ml) and brine (300 ml). The organic layer is dried, evaporated and the residue is chromatographed (flash-silica gel column eluting with 4 to 1 toluene/ethylacetate to yield 800 mg of 1,18-bis-[(1-naphthyl)methyl]-1,5,14,18-tetra(t-butoxycarbonyl)-1,5,14,18-tetraazaoctadecane.

Step B: The product of Step A (800 mg) is dissolved in methanol (50 ml), excess HCl is added and the resulting mixture stirred overnight at ambient temperature. The mixture is filtered, the solids vacuum dried to yield the desired product of this example, mp 262°–264° C.

Illustrative Examples for Reaction Scheme B

EXAMPLE 3

1,20-Bis[(phenyl)methyl]-1,16,15,20-tetraazaeicosane●4 HCl

Step A: N,N'-Bis(t-butoxycarbonyl)-1,8-octanediamine

Dissolve 10.8 gm (0.075) of diaminooctane in 200 ml $CH_2Cl_2$ and 100 ml $CH_3OH$, add 32.7 gm (0.156 mol) of di-t-butyldicarbonate and stir the mixture overnight. Evaporate, in vacuo, and crystallize the residue from hexane to obtain 20.2 gm of the desired compound, mp 96°–97° C.

Step B: 4-[[(Phenyl)methyl]amino]-butan-1-ol

Combine 4-amino-butan-1-ol (8.9 gm - 0.1 mol), benzaldehyde (10.6 gm - 0.1 mol), EtOH (100 ml) and $PtO_2$ (0.3 gm), and hydrogenate the mixture at 45 lbs./sq.in. until $H_2$ is no longer taken up. Filter, evaporate the solvent (in vacuo) to yield 17.7 gm of the desired compound. Rf is 0.70 (eluted from silica gel with 10% conc. $NH_3$/$CH_3OH$).

Step C: 4-[N-(t-butoxycarbonyl)-N-[(phenyl)methyl]-amino]butan-1-ol

Combine the butanol of Step B (17.7 g - 0.1 mol) and di-t-butyldicarbonate in 100 ml of $CH_2Cl_2$ and stir the mixture overnight. Evaporate off the solvents, in vacuo, and flash chromatograph the residue, eluting from silica gel with 25% EtOAc/hexane to obtain the desired compound. Rf is 0.27 (silica gel plates eluted with 20% EtOAc/hexane).

Step D: 4-[N-(t-butoxycarbonyl)-N-[(phenyl)methyl]-amino]-1-methansulfonyl butane Cool (ice-bath) a mixture containing the product of Step C (21.8 gm - 0.078 mol), 250 ml $CH_2Cl_2$ and 9.7 ml pyridine (0.12 mol), add in a dropwise fashion (20 minutes) mesylchloride (6.65 ml - 0.086 mol) in 6.6 ml $CH_2Cl_2$ and allow the mixture to warm to room temperature, stirring the mixture for 2 hours. Pour the resulting mixture into 200 ml $CH_2Cl_2$, wash with 500 ml 0.5N HCl, saturated $NaHCO_3$, dry over $MgSO_4$, evaporate (in vacuo) and flash chromatograph eluting from the silica gel with 25% EtOAc/hexane to obtain 10.7 g of desired product. Rf is 0.36 (silica gel plates eluted with 25% EtOAc/hexane).

Step E: 1,20-Bis[(phenyl)methyl]-1,16,15,20-tetra-(t-butoxycarbonyl)-1,6,15,20-tetraazaeicosane Admix the products of Step A (5.16 gm - 0.015 mol) and of Step D of this example (10.7 g - 0.032 mol), Kt-BuO (3.92 gm), NaI (0.2 gm), and 60 ml DMF and stir the mixture for 72 hours at room temperature. Evaporate off the solvent (in vacuo), take up the residue in 600 ml EtOAc and wash (2×) with 200 ml water. Dry the organic layer ($MgSO_4$), evaporate the solvents, and flash chromatograph the viscous residue on silica gel eluting with 20% EtOAc/hexane to obtain the desired product, Rf is 0.22 (silica gel plates eluted with 20% EtOAc/hexane).

Step F: 1,20-Bis[(phenyl)methyl]-1,6,15,20-tetraeicosane●4HCl

Dissolve the product of Step E (4.7 gm) (0.0054 mol) in 5 ml EtOH and treat with 54 ml of 2N HCl in $EtO_2$, stir the mixture overnight, filter and recrystallize to so-obtained solids from isopropanol/water. Cool, filter and dry the desired product, mp >300° C., Rf is 0.47 (eluted from silica with 10% conc. $NH_3$/$CH_3OH$).

Illustrative Examples for Reaction Scheme C

EXAMPLE 4

1,4,13,16-Tetra(t-butoxycarbonyl)-1,4-13,16-tetraazahexadecane

Combine 4.75 gm 1,8-dibromooctane (0.017 mol), 20 ml EtOH and 9.32 ml of ethylene diamine and reflux the mixture overnight. Cool and treat the mixture with 1.4 gm NaOH. Evaporate off the solvent and triturate the residue with $CH_2Cl_2$ (200 ml 2×), filter. Treat the filtrate with 66.6 gm of di-t-butyldicarbonate and stir the mixture overnight. Remove the solvent and subject the residue to flash chromatography, eluted with 25% EtOAc/hexane to yield the desired product. Rf is 0.64 eluted from silica gel with 50% EtOAc/hexane.

The foregoing may be bis-N-alkylated and the product deprotected by methods analogous to Steps D and E of Example 1 to produce desired compounds of the Formula R'HN(CH$_2$)$_2$N(CH$_2$)$_8$N(CH$_2$)$_2$NHR', e.g., 1,16-Bis[(phenyl)methyl]-1,4,13,16-tetraazahexadecane●4 HCl.

Illustrative Example for Reaction Scheme D

EXAMPLE 5

1,18-Bis[(2-phenyl)ethyl]-1,5,14,18-tetraazaoctadecane●4 HCl

Step A: 1,18-Bis[[(phenyl)methyl]carbonyl]-5,14-bis-[(phenyl)methyl]-1,5,14,18-tetraazaoctadecane Chill a solution of 5,14-bis[(phenyl)methyl]-1,5,14,18-tetraazaoctadecane (2.2 g, 5 mmole) and triethylamine (2 g, 20 mmole) in chloroform (100 ml) in an ice bath. Add a solution of phenylacetyl chloride (2.3 g, 15 mmole) in chloroform (10 ml) dropwise. Remove the ice bath and stir the mixture at ambient temperature for 18 hours. Extract the reaction mixture with aqueous sodium bicarbonate, dry the organic layer and evaporate. Chromatograph the residue on a flash silica gel column (ethyl acetate) to give 3 g of the desired product as a thick oil.

Step B: Add a solution of the product of Step A in THF (150 ml) dropwise to a suspension of LAH (0.5 g) in THF (500 ml). Stir the mixture for 48 hours at ambient temperature. Decompose the excess reducing agent by dropwise addition of 1 ml of water, 1 ml of 15% NaOH then 3 ml of water. Filter the mixture and evaporate the filtrate. Take the residue up in ethanol (100 ml) and add anhydrous HCl gas to convert the product, 1,18-bis[(phenyl)ethyl]-5,14-bis-[(phenyl)methyl]-1,5,14,18-tetraazaoctadecane, to its tetrahydrochloride salt. Hydrogenate this product in ethanol (150 ml) in the presence of Pearlman's catalyst (0.3 g) at 43 psig on a Parr hydrogenation apparatus for 24 hours.

Filter off the catalyst and evaporate the filtrate. Crystallize the residue from 2-propanol to give the product 1,18-bis-[(phenyl)ethyl]-1,5,14,18-tetraazaoctadecane tetrahydrochloride salt hemihydrate, mp 228°–231° C.

Alternative Reductive Alkylation Procedures

EXAMPLE 6

1,14-Bis[(phenyl)methyl]-1,5,10,14-tetraazatetradecane●4 HCl

Combine spermine (2.02 gm), 2.13 ml of benzaldehyde, 40 ml of EtOH and 0.1 gm of $PtO_2$, treat the mixture with $H_2$ (45 lbs./sq.in.) until $H_2$ is no longer taken up. Remove the catalyst by filtration, add 100 ml 1N HCl in EtOH, add water until solids dissolve, add isopropanol until solution becomes turbid. Cool and filter, and dry the resulting solid to yield 2.0 of the desired product mp >290° C. Rf is 0.50 (eluted from silica gel with 20% conc. $NH_3/CH_3OH$).

EXAMPLE 7

1,18-Bis-[(methylthiophenyl)methyl]-1,5,14,18-tetraazaoctadecane●4 HCl

Combine 0.81 gm of the product B of example 1, 0.05 gm $Na_2CO_3$, 0.25 gm $NaBH_3CN$ and 0.53 ml of 4-methylthiobenzaldehyde in 100 ml $CH_3OH$ and stir the mixture overnight at room temperature. Pour the reaction mixture into 300 ml $CH_2Cl_2$, wash with 100 ml of 1N NaOH and 100 ml of saturated NaCl, dry over $MgSO_4$ and evaporate in vacuo. Recrystallize the so-obtained crude product from EtOAc, cool, filter and treat with 10 ml EtOH and 30 ml of 2N HCl in $Et_2O$. Filter and dry the so-obtained solid to obtain 0.32 gm of the desired product. Rf is 0.58 (eluted from silica gel with 40% conc. $NH_3/CH_3OH$).

Illustrative Example of Reaction Scheme E

EXAMPLE 8

1,18-Bis(phenyl)-1,5,14,18-tetraazaoctadecane
Step A: N-(Phenyl-N,N'-bis(t-butoxycarbonyl) propanediamine
Cool 200 ml of anhydrous $Et_2O$ in an ice bath and add lithium aluminum hydride (8.74 gm -0.23 mol). Add, in a dropwise fashion over 30 minutes, 3-anilinopropionitrile (14.6 gm) in 50 ml of $Et_2O$, remove the ice bath, and reflux the resulting mixture overnight. Sequentially add 8.7 ml of water, 1.5 g of NaOH (in 10 ml of water) and 25 ml of water. Filter the resulting ppt, rinse with 200 ml of $Et_2O$ and remove the solvent, in vacuo, and treat the resulting N-(phenyl) propanediamine with 43.6 g of di-t-butyldicarbonate in 600 ml of $CH_2Cl_2$. After stirring overnight, evaporate off the solvent and subject the residue to flash chromatography from silica gel eluting with 17% EtOAc/hexane to produce the desired compound. Rf is 0.50 (eluted from silica gel with 25% EtOAc/hexane).
Step B: 1,18-Bis(phenyl)-1,5,14,18-tetra(t-butoxycarbonyl)-1,5,14,18-tetraazaoctadecane
Stir a mixture containing the product of Step A (13.0 gm), diiodooctane 3.70 gm) and 4.14 g of potassium t-butoxide in 200 ml of DMF for about 16 hours. Evaporate the solvent at 0.5 mm and 45° C., take up the residue in 800 ml of EtOAc. Wash (2×) with 300 ml of water, dry (MgSO_4) and remove the solvent in vacuo. Subject the so-obtained viscous oil to flash chromatography, eluting with 15% EtOAc from silica gel to yield 5.7 g of the desired product. Rf of 0.36 (eluted from silica gel with EtOAc/hexane). Remove the N-boc protecting groups according to the procedure of Step E of Example 1 to produce the title compound of this example. mp 264°–267° C.

Illustrative Examples of Reaction Scheme F

EXAMPLE 9

1,18-Bis(2,3-butadienyl)-1,5,14,18-tetraazaoctadecane tetrahydrochloride
Step A: N-(t-Butoxycarbonyl)propargylamine
In a dropwise fashion, add propargylamine (25 gm) in 25 ml of $CH_2Cl_2$ to a stirring mixture of di-t-butyldicarbonate (99.18 gm) in 900 ml of $CH_2Cl_2$. After 2 hours, remove the solvent, in vacuo, to obtain 70 gm of the desired N-protected propargylamine.
Step B: N-(t-Butoxycarbonyl)-2,3-butadienylamine
Reflux a mixture containing N-(t-butoxycarbonyl)-propargylamine (70 gm), 93.5 ml of 32% formaldehyde, 76.4 ml of diisopropylamine, 19.66 gm of cuprous bromide and 860 ml of p-dioxane for 12 hours. Cool and dilute the resulting mixture with 3000 ml of $Et_2O$, wash with 500 ml of water, 1000 ml acetic acid, 500 ml of water (2×), 200 ml sat'd. sodium chloride, dry (MgSO_4) and evaporate in vacuo. Flash chromatograph the residue eluting from silica gel with 10% $Et_2O$/hexane to yield 40.8 g of the desired compound. Rf is 0.31 (eluted from silica gel with 10% EtOAc/hexane).
Step C: N,N-Bis[(phenyl)methyl]-1,8-diaminooctane
Combine 14.4 gm of diaminooctane, 20.3 ml of benzaldehyde and 0.66 gm of $Pt_2O$ in 100 ml of ethanol. Treat the resulting mixture with hydrogen at 45 lbs./sq.in. until no further hydrogen is taken up. Filter, evaporate the solvent (in vacuo), and distill the rendered material to obtain 25.5 gm of the desired product, bp 185°–190° C. at 0.1 mm.
Step D: 1,18-Bis(hydroxy)-5,14-bis[(phenyl)methyl]-5,14-diazaoctadecane
Reflux a mixture containing 25.5 g of the product of Step C, 13.2 ml of 3-chloro-1-hydroxy-propane, 50.4 gm of $Na_2CO_3$ and 1.19 gm of sodium iodide in 40 ml of n-butanol for 18 hours. Cool the mixture and pour into 700 ml of ethylacetate, wash with water, dry over $MgSO_4$ and remove the solvent (in vacuo) to obtain a residue which upon distillation yields 30.0 gm of the desired product, bp 250°–252° C. at 0.1 mm.
Step E: 1,18-Bis(hydroxy)-5,14-diazaoctadecane
Hydrogenate a mixture containing 3.0 gm of the product of Step D, 30 ml of AcOH and 0.6 gm of palladium oxide at 45 lbs./sq.in. until no further hydrogen is taken up. Filter and remove the solvent (in vacuo) to yield 1.77 gm of the desired product. Rf is 0.37 (eluted from silica gel with 10% conc. $NH_3/CH_3OH$).
Step F: 1,18-Bis(hydroxy)-5,14-bis-(t-butoxycarbonyl)-5,14-diazaoctadecane
Stir a mixture containing 1.77 gm of the product of Step E, 2.97 gm (0.0136 mol) of di-t-butyldicarbonate, 3 ml of triethylamine and 50 ml of $CH_2Cl_2$ overnight. Dilute the mixture with 200 ml of $CH_2Cl_2$, wash with 200 ml of 0.5N HCl, and then 100 ml of sat'd NaCl, dry (over $MgSO_4$) and remove the solvent (in vacuo). Flash chromatograph the residue, eluting from silica gel with 75% EtOAc to obtain the desired product, Rf 0.29, (eluted from silica gel with 75% EtOAc/hexane).
Step G: 1,18-Bis(methansulfonyl)-5,14-bis(t-butoxycarbonyl)-5,14-diazaoctadecane Cool to 0° C. a mixture containing 3.0 gm of the product of Step F, 3.3 ml of triethylamine and 70 ml of $CH_2Cl_2$. In a dropwise fashion add 1.22 ml of mesylchloride in 10 ml of $CH_2Cl_2$, and stir the resulting mixture at 0° C. for 1½ hours. Pour the mixture into 100 ml of $CH_2Cl_2$, wash with 200 ml of 1N AcOH, 100 ml of water, 100 ml of sat'd sodium bicarbonate, dry over $MgSO_4$ and remove the solvent in vacuo. Flash chromatograph the residue, eluting from silica gel with 60% EtOAc/hexane to obtain 3.5 gm of the desired product. Rf is 0.39.

Step H: 1,18-Bis(2,3-butadienyl)-1,5,14,18-tetra-(t-butoxycarbonyl)-1,5,14,18-tetraazaoctadecane Combine a mixture containing 3.5 gm of the product of Step G, 1.74 gm of sodium iodide, 0.51 gm of hexane washed sodium hydride (60% in oil) in 12 ml of DMF with 2.16 gm of N-(t-butoxycarbonyl)-2,3-butandienylamine (i.e., the product of Step B) and allow the resulting mixture to stand for 2 hours. Remove the solvent (in vacuo), add 350 ml of ethyl acetate to the residue, wash with 50 ml of water (4×), 100 ml sat'd sodium chloride and dry over $MgSO_4$. Remove the solvents (in vacuo) and flash chromatograph the residue from silica gel eluting with 30% EtOAc/hexane to yield 0.5 gm of the desired product, as a viscous oil. Rf is 0.39 (eluting from silica gel with 25% EtOAc/hexane).

Step I: 1,18-Bis(2,3-butadienyl)-1,5,14,18-tetraazaoctadecane•4 HCl

Dissolve 0.5 gm of the product of Step H in 2 ml of EtOH and while stirring treat the mixture with 10 ml of 2N HCl in $Et_2O$. Stir the resulting mixture overnight, filter and dry the solids (in vacuo) to obtain 0.22 gm of the desired product, mp 283°–284° C. dec. Using the abbreviated form for naming the compounds embraced by formula I, it is to be noted that the following specific compounds are readily prepared by applying the foregoing described techniques and procedures and by applying known prior art principles to achieve the necessary modifications:

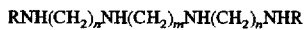

wherein the R groups are the terminal R groups and the moiety between these R groups is the "polyamine moiety".

| Polyamine Moiety | Terminal R Moieties |
| --- | --- |
| 3-8-3 | bis-methyl |
| 3-8-3 | bis-ethyl |
| 3-8-3 | bis-propyl |
| 3-8-3 | bis-butyl |
| 3-8-3 | bis-t-butyl |
| 3-8-3 | bis-phenyl |
| 3-8-3 | bis-naphthyl |
| 3-8-3 | bis-[(phenyl)methyl] |
| 3-8-3 | bis-[(phenyl)ethyl] |
| 3-8-3 | bis-[(naphthyl)methyl] |
| 3-8-3 | bis-[(1-naphthyl)ethyl] |
| 3-8-3 | bis-[(4-chlorophenyl)methyl] |
| 3-8-3 | bis-[(4-hydroxyphenyl)methyl] |
| 3-8-3 | bis-[(4-methoxyphenyl)methyl] |
| 3-8-3 | bis-[(4-methylphenyl)methyl] |
| 3-8-3 | bis-[(4-methylthio)methyl] |
| 3-8-3 | bis-[(4-methylsulfinyl)methyl] |
| 3-8-3 | bis-[(4-methylsulfonyl)methyl] |
| 3-8-3 | bis-(acetylenyl) |
| 3-8-3 | bis-(2,3-butadienyl) |
| 3-8-3 | bis-allyl |
| 3-8-3 | bis-allenyl | as well as their 2-8-2, 4-8-4, 5-8-5 and 6-8-6 analogs, and the analogs thereof wherein the polyamine moiety is as specifically mentioned in the following chart:

| Polyamine Moiety | | | | |
| --- | --- | --- | --- | --- |
| 2-4-2 | 3-4-3 | 4-4-4 | 5-4-5 | 6-4-6 |
| 2-5-2 | 3-5-3 | 4-5-4 | 5-5-5 | 6-5-6 |
| 2-6-2 | 3-6-3 | 4-6-4 | 5-6-5 | 6-6-6 |
| 2-7-2 | 3-7-3 | 4-7-4 | 5-7-5 | 6-7-6 |
| 2-9-2 | 3-9-3 | 4-9-4 | 5-9-5 | 6-9-6 |
| 2-10-2 | 3-10-3 | 4-10-4 | 5-10-5 | 6-10-6 |
| 2-11-2 | 3-11-3 | 4-11-4 | 5-11-5 | 6-11-6 |
| 2-12-2 | 3-12-3 | 4-12-4 | 5-12-5 | 6-12-6 |

In their end-use application, the compounds of this invention are found to be useful in treating diseases caused by protozoal infections. In this end-use application it is also to be found that the use of conjunctive therapy with either an ornithine decarboxylase inhibitor or an arginine decarboxylase inhibitor will aid in the efficiency of the treatment of the particular disease state being treated.

In its generic concept the compounds of this invention (I) are useful in treating diseases caused by protozoal parasites, living either intracellularly or extracellularly in a mammalian host to be treated. Inclusive of such protozoa are parasites categorized in such genera as: Plasmodium (e.g., including such species as vivax, malariae, ovale, falciparum, knowlesi, berghei, vinckei, chabaudi, gallinaceum and lophurae), Leishamania (e.g., such species as donovani, tropica, braziliensis and mexicana), Babesia (e.g., such species as bovis, rodhaini and microti), Trypanosoma (of the class stercoraria) (e.g., such species as cruzi, it is being noted that this species is an example of a trypansome which utilizes arginine decarboxylase in its polyamine metabolic pathways and therefore conjunctive therapy would be with an ADC inhibitor), Toxoplasma (e.g., such species as gondii) and Theileria (e.g., parva). Protozoal parasites which live outside of the blood cells include trypanosoma (of the class slaivaria) (e.g., such species as rhodesiense, gambiense, brucei, evansi, equinum, equiperdum, congolense, and vivax), Trichomonas (e.g., species such as faginalis, foetus and gallinae), Entamoeba (e.g., such as histolytica and invadens), Pneumocystis carinii, Eimeria (E.g., tenella, necatrix and Brunetti), Cryptosporidia and Giardia (e.g., lamblia).

All of the foregoing protozoa are known to infect animals and the particular diseases for which these protozoa are responsible are well known. Thus within the scope of this invention is the use of the compounds of formula I, with or without the conjunctive use of the appropriate ornithine or arginine decarboxylase inhibitors, in the treatment of the diseases caused by the foregoing protozoa. Important human disease states for which there is a need for new therapy are Amebiasis, Malaria, Leishmaniasis, Trypanosomiasis, Toxoplasmosis, as well as the so-called opportunistic infection diseases such as Pneumocystis carinii.

As is well known, malaria remains the world's most important infection in terms of human suffering and death. Even today, there is a desperate need for practical, effective and safe drugs to combat this protozoal infection for, despite the pronounced advances in treatment of malaria, transmission of malaria is rising, multidrug-resistant strains of Plasmodium falciparum are spreading, and the degree of resistance to drugs of this most dangerous and prevalent plasmodial species is increasing. Indeed it has been stated that over 200 million people have malaria and over one million deaths per year are associated with malaria in Africa alone, and it is known that travel to and from those endemic regions poses an expanding health problem. Thus, a particularly important aspect of this invention is the use of the compounds of this invention (I), efficiently enhanced with conjunctive therapy with an ornithine decarboxylase inhibitor, in the treatment of malaria, including, but not limited to, such specifics as vivax and ovale malaria, falciparum malaria, (including cerebral malaria), malariae malaria, and blackwater fever and algid malaria.

On the basis of standard laboratory procedures (both in vitro and in vivo) well known for the evaluation of compounds useful for the treatment of protozoal infections, as well as by comparisons with known anti-protozoal agents (e.g., chloroquin) the compounds of formula I are effective in the treatment of the protozoal diseases at doses of about 1 to 100 mg per kilogram of body weight per day. The preferred dose is about 10 to 30 mg/kg when administered parenterally and about 3 to 5 times that when administered enterally. Preferably the compounds, in the initial phases of treatment, are administered 3 times daily for about three days, followed by continued treatment once a day until laboratory analysis shows a cure. The preferred method of administration is intramuscularly.

Suitable ornithine decarboxylase inhibitors are such compounds as α-difluoromethylornithine, and α-monofluoromethylornithine, although other well known ODC inhibitors may also be utilized. Suitable arginine decarboxylase inhibitors are the mono- and difluoromethyl arginine compounds; the ODC and ADC inhibitors being known and available to those skilled in the art. Of course it logically follows that when any particular protozoa utilizes the arginine decarboxylase enzyme in its polyamine metabolic pathway then conjunctive therapy would utilize the ADC inhibitors; similarly when the infecting protozoa utilizes ornithine decarboxylase enzyme in its polyamine metabolic pathway the conjunctive therapy would employ and ODC inhibitor. When used the ODC and ADC inhibitors would be useful at about 50 to 500 mg/kg of bodyweight per day, generally extrapolated to about 10–20 gms per 70 kgm patient. In the conjunctive therapy the inhibitors would be administered at the start of the treatment with the novel polyamines of formula I and would be administered so as to maintain a suitable blood level during the entire course of treatment. Depending upon the state of the patient to be treated as judged by attending diagnostician, the ODC or ADC inhibitors preferably are administered intravenously or as solutions suitable for drinking. In practice the anti-protozoal polyamine and the arginine or ornithine decarboxylase inhibitors will not be administered in one pharmaceutical preparation. Rather it is preferred to co-administer these components as separate entities. For example, it may be preferred to administer the polyamine (I) in three equal doses, while it would be preferred to administer the decarboxylase inhibitor(s) twice daily. The important aspect to the treatment is that both medicaments be used in conjunction with each other. The most effective manner in treating the diseases with the polyamine (I) is with conjunctive therapy with the appropriate decarboxylase inhibitor.

The appropriate pharmaceutical formulations for the enteral and parenteral administrations may be prepared by procedures well known in the art such as preparing sterile physiologically acceptable solutions suitable for intramuscular injections.

As is well known in the art of pharmaceutical inventions wherein generic classes of compounds are involved, certain sub-generic and certain specific compounds are more efficient in their end-use applications than other members of the generic class. In this invention, those compounds having a center alkylene chain of 6 to 9 carbon atoms are preferred, particularly those having six, seven and eight carbon atoms.

Also preferred are those compounds wherein the alkylene chains which are on either side of the center alkylene chain are those having two, three or four carbon atoms, with three being most preferred. Thus the most preferred compounds are those wherein the polyamine moiety has a 3-6-3, a 3-7-3, a 3-8-3, a 3-9-3, a 2-6-2, a 2-7-2, a 2-8-2, a 2-9-2, a 4-6-4, a 4-7-4, a 4-8-4, or a 4-9-4 constitution. The preferred are the 3-6-3, the 3-7-3, the 3-8-3, and 3-9-3, with 3-7-3 and 3-6-3 being most preferred. The preferred terminal R group is ethyl or benzyl, the compound preferably being a bis-ethyl or a bis-benzyl. In all instances it has been shown that the symmetrical compounds are preferred. The most preferred is a bis-benzyl-3-7-3 or a bis-ethyl-3-7-3 . In those instances wherein R is an alkyl radical methyl or ethyl are preferred.

The most preferred ornithine decarboxylase inhibitor is α-difluoromethyl ornithine and the most preferred arginine decarboxylase inhibitor is α-difluoromethyl arginine.

We claim:

1. A compound of the formula:

and the pharmaceutically acceptable salts thereof wherein n is an integer 2 to 4, m is an integer 7, and R is —(CH$_2$)$_x$(Ar)—X wherein x is zero, one, or two, Ar is phenyl or naphthyl, and X is C$_1$–C$_6$ alkoxy, halogen, C$_1$–C$_4$ alkyl, —S(O)$_x$R$_1$ with R$_1$ being C$_1$–C$_6$ alkyl.

2. A compound of claim 1 wherein n is three.

3. A compound of claim 1 wherein R is benzyl.

4. A compound of claim 1 wherein R is phenyl.

5. A compound of claim 1 wherein R is phenylethyl.

6. A compound of claim 1 wherein said compound is N,N'-bis[3-[(phenylmethyl)amino]propyl]-1,7-heptanediamine.

7. A method for treating infection caused by protozoa which comprises administering a therapeutically effective quantity of a compound of of the formula:

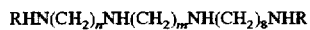

and the pharmaceutically acceptable salts thereof wherein n is an integer 2 to 4, m is an integer 6 to 12 and R is —(CH$_2$)$_x$(Ar)—X wherein x is zero, one, or two, Ar is phenyl or naphthyl, and X is H, C$_1$–C$_6$ alkoxy, halogen, C$_1$–C$_4$ alkyl, —S(O)$_x$R$_1$ being C$_1$–C$_6$ alkyl.

8. A method according to claim 7 wherein said treatment is conjunctive with an ornithine decarboxylase inhibitor or an arginine decarboxylase inhibitor.

9. A method according to claim 7 wherein the infection is caused by protozoa of the genera consisting of Plasmodium, Trypanosoma, including salivaria and stercoraria, Leishmania, Trichomonas, Babesia, Toxoplasma, and Theileria.

10. A method according to claim 9 wherein the treatment is conjunctive with an ornithine decarboxylase inhibitor or an arginine decarboxylase inhibitor.

11. A method according to claim 9 wherein the host suffering from a protozoal infection is suffering from malaria.

12. A method according to claim 9 wherein the host suffering from a protozoal infection is suffering from Chaga's Disease.

13. A method according to claim 11 wherein the treatment utilizes α-difluoromethyl ornithine in its conjunctive therapy.

14. A method according to claim 12 wherein the treatment utilizes α-difluoromethyl arginine in its conjunctive therapy.

15. A method according to claim 13 wherein the polyamine is N,N'-bis[3-[(phenylmethyl)amino]propyl]-1,7-heptanediamine.

16. A method according to claim 13 wherein the polyamine is N,N'-bis[(phenylmethyl)amino]propyl]-1,6-hexanediamine.

17. A compound of the formula:

$$RHN(CH_2)_nNH(CH_2)_mNH(CH_2)_nNHR$$

and the pharmaceutically acceptable salts thereof wherein n is an integer 2 to 4, m is an integer 8 to 11, and R is —$(CH_2)_x(Ar)$—X wherein x is zero, one, or two, Ar is phenyl or naphthyl, and X is $C_1$–$C_6$ alkoxy, halogen, $C_1$–$C_4$ alkyl, —$S(O)_xR_1$ with $R_1$ being $C_1$–$C_6$ alkyl.

18. A compound of claim 17 wherein m is an integer 8 to 10.

19. A compound of the formula:

$$RHN(CH_2)_nNH(CH_2)_mNH(CH_2)_nNHR$$

and the pharmaceutically acceptable salts thereof wherein n is an integer 2 to 4, m is 6, and R is —$(CH_2)_x(Ar)$13 X wherein x is zero, one, or two, Ar is phenyl or naphthyl, and X is $C_1$–$C_6$ alkoxy, halogen, $C_1$–$C_4$ alkyl, —$S(O)_xR_1$ with $R_1$ being $C_1$–$C_6$ alkyl.

20. A compound of claim 19 wherein n is 3.
21. The method of claim 7 wherein m is 6.
22. The method of claim 7 wherein m is 7.
23. The method of claim 7 wherein m is 8.
24. The method of claim 7 wherein m is 9.
25. The method of claim 7 wherein m is 10.
26. The method of claim 7 wherein m is 11.
27. The method of claim 7 wherein m is 12.
28. The method of any one of claims 21 to 27 wherein n is 3.
29. The method of any one of claims 21–27 wherein R is benzyl.

30. A compound of the formula:

$$RHN(CH_2)_nNH(CH_2)_mNH(CH_2)_nNHR$$

and the pharmaceutically acceptable salts thereof wherein n is an integer 2 to 4, m is 12, and R is —$(CH_2)_x(Ar)$13 X wherein x is zero, one, or two, Ar is phenyl or naphthyl, and X is H, $C_1$–$C_6$ alkoxy, halogen, $C_1$–$C_4$ alkyl, —$S(O)_xR_1$ with $R_1$ being $C_1$–$C_6$ alkyl.

31. A compound of claim 30 wherein n is 3.

* * * * *